(12) United States Patent
Lin et al.

(10) Patent No.: US 7,888,530 B2
(45) Date of Patent: Feb. 15, 2011

(54) OPTIMIZED PRODUCTION OF AROMATIC DICARBOXYLIC ACIDS

(75) Inventors: Robert Lin, Kingsport, TN (US); Marcel de Vreede, Barendrecht (NL)

(73) Assignee: Eastman Chemical Company, Kingsport, TN (US)

( * ) Notice: Subject to any disclaimer, the term of this patent is extended or adjusted under 35 U.S.C. 154(b) by 278 days.

(21) Appl. No.: 11/181,449

(22) Filed: Jul. 14, 2005

(65) Prior Publication Data
US 2006/0047165 A1 Mar. 2, 2006

Related U.S. Application Data

(60) Provisional application No. 60/606,585, filed on Sep. 2, 2004.

(51) Int. Cl.
*C07C 51/16* (2006.01)
(52) U.S. Cl. .............. 562/412; 562/405; 562/407; 562/408; 562/409; 562/416
(58) Field of Classification Search ............... 562/405, 562/407, 408, 409, 412, 414
See application file for complete search history.

(56) References Cited

U.S. PATENT DOCUMENTS

| | | | |
|---|---|---|---|
| 2,964,559 A | 12/1960 | Burney et al. |
| 3,840,641 A | 10/1974 | Wampfler et al. |
| 3,873,468 A | 3/1975 | Kobinata et al. |
| 3,950,409 A | 4/1976 | Yokota et al. |
| 3,996,271 A | 12/1976 | Yokota et al. |
| 4,081,464 A | 3/1978 | Marsh et al. |
| 4,158,738 A | 6/1979 | Scott et al. |
| 4,185,073 A | 1/1980 | Marsh et al. |
| 4,219,669 A | 8/1980 | Tsuchiya et al. |
| 4,298,580 A | 11/1981 | Harper et al. |
| 4,330,676 A | 5/1982 | Moxham |
| 4,356,319 A | 10/1982 | Roffia et al. |
| 4,769,489 A | 9/1988 | Abrams et al. |
| 4,892,972 A | 1/1990 | Schroeder et al. |
| 4,914,230 A | 4/1990 | Abrams et al. |
| 4,939,297 A | 7/1990 | Browder et al. |
| 5,200,557 A | 4/1993 | Gee et al. |
| 5,643,468 A | 7/1997 | Ure |
| 5,676,847 A | 10/1997 | Yamamoto et al. |
| 5,705,682 A | 1/1998 | Ohkoshi et al. |
| 5,770,765 A | 6/1998 | Ohkoshi |
| 5,840,965 A | 11/1998 | Turner et al. |
| 5,916,422 A | 6/1999 | Kimura et al. |
| 5,955,394 A | 9/1999 | Kelly |
| 5,973,196 A | 10/1999 | Takano et al. |
| 5,994,567 A | 11/1999 | Kingsley et al. |
| 6,054,610 A | 4/2000 | Lee et al. |
| 6,133,476 A | 10/2000 | Lin |
| 6,137,001 A | 10/2000 | Broeker et al. |
| 6,153,790 A | 11/2000 | June et al. |
| 6,562,997 B2 | 5/2003 | Sikkenga et al. |
| 7,074,954 B2 | 7/2006 | Sheppard et al. |
| 7,132,566 B2 | 11/2006 | Sumner, Jr. et al. |
| 7,273,559 B2 | 9/2007 | Gibson et al. |
| 7,291,270 B2 | 11/2007 | Gibson et al. |
| 2001/0041811 A1 | 11/2001 | Sikkenga et al. |
| 2002/0016500 A1 | 2/2002 | Matsumoto et al. |
| 2002/0193630 A1* | 12/2002 | Lin et al. ............ 562/414 |
| 2004/0225148 A1 | 11/2004 | Isogai et al. |
| 2004/0244536 A1 | 12/2004 | Lin |
| 2004/0245176 A1 | 12/2004 | Parker et al. |
| 2004/0249207 A1 | 12/2004 | Lin et al. |
| 2004/0249208 A1 | 12/2004 | Lin et al. |
| 2007/0205153 A1 | 9/2007 | Parker et al. |
| 2007/0208195 A1 | 9/2007 | Gibson et al. |
| 2007/0208196 A1 | 9/2007 | Parker et al. |
| 2007/0208197 A1 | 9/2007 | Gibson et al. |
| 2007/0208198 A1 | 9/2007 | Parker et al. |
| 2007/0208199 A1 | 9/2007 | Parker et al. |
| 2007/0213557 A1 | 9/2007 | Seiki et al. |
| 2008/0103333 A1 | 5/2008 | Nubel et al. |

FOREIGN PATENT DOCUMENTS

| | | |
|---|---|---|
| DE | 2131470 A | 6/1970 |
| EP | 0 181 127 A2 | 5/1986 |
| EP | 0 764 627 A1 | 3/1997 |
| EP | 0 579 715 B1 | 8/1997 |
| EP | 1 484 305 A1 | 8/2004 |
| EP | 1 484 306 A1 | 8/2004 |

(Continued)

OTHER PUBLICATIONS

USPTO office action dated Nov. 30, 2006 for copending U.S. Appl. No. 10/975,256.

(Continued)

*Primary Examiner*—Sudhakar Katakam
(74) *Attorney, Agent, or Firm*—Steven A. Owen; Bernard J. Graves, Jr.

(57) ABSTRACT

Disclosed is an optimized process and apparatus for more efficiently producing aromatic dicarboxylic acids (e.g., terephthalic acid). In one embodiment the process/apparatus reduces costs by recovering and purifying residual terephthalic acid present in the liquid phase of an initial oxidation slurry. In another embodiment the process apparatus reduces costs associated with hydrogenation by forming a final composite product containing unhydrogenated acid particles.

15 Claims, 3 Drawing Sheets

FOREIGN PATENT DOCUMENTS

| | | |
|---|---|---|
| GB | 892766 | 3/1962 |
| GB | 1407705 | 9/1975 |
| GB | 2067563 | 7/1981 |
| JP | 46-14339 B | 11/1974 |
| JP | 51-145488 A | 12/1976 |
| JP | 49-123191 A | 2/1979 |
| JP | 54-25292 A | 2/1979 |
| JP | 62-25651 B2 | 6/1987 |
| JP | 09-048744 A | 2/1997 |
| JP | 9-157214 A | 6/1997 |
| JP | 10-114699 A | 5/1998 |
| JP | 11-349529 A | 12/1999 |
| JP | 3211396 B2 | 9/2001 |
| JP | 3232678 B2 | 11/2001 |
| JP | 59-53441 A | 3/2004 |
| KR | 1991-5989 B1 | 8/1991 |
| WO | WO 92/18453 | 10/1992 |
| WO | WO 92/18454 A1 | 10/1992 |
| WO | WO 93/24441 A | 12/1993 |
| WO | WO 97/27168 A1 | 7/1997 |
| WO | WO 97/30963 A | 8/1997 |
| WO | WO 00/31014 A1 | 6/2000 |
| WO | WO 01/55075 A2 | 8/2001 |
| WO | 2004074231 A1 | 9/2004 |

OTHER PUBLICATIONS

USPTO office action dated Nov. 30, 2006 for copending U.S. Appl. No. 10/975,252.
USPTO Notice of Allowance dated Jan. 15, 2008 for copending U.S. Appl. No. 10/455,016.
USPTO office action dated Jan. 18, 2007 for copending U.S. Appl. No. 10/455,017.
USPTO Office Action dated Feb. 14, 2008 for copending U.S. Appl. No. 11/842,469.
Copending U.S. Appl. No. 11/655,395 filed Jan. 19, 2007, Philip E. Gibson et al.
Copending U.S. Appl. No. 11/655,317 filed Jan. 19, 2007, Philip E. Gibson et al.
Copending U.S. Appl. No. 11/655,396 filed Jan. 19, 2007, Kenny R. Parker et al.
USPTO Office Action dated Mar. 4, 2008 for copending U.S. Appl. No. 11/839,575.
USPTO Office Action dated Mar. 5, 2008 for copending U.S. Appl. No. 11/655,317.
USPTO Office Action dated Mar. 4, 2008 for copending U.S. Appl. No. 11/839,578.
USPTO Office Action dated Mar. 5, 2008 for copending U.S. Appl. No. 11/655,396.
USPTO Office Action dated Mar. 7, 2008 for copending U.S. Appl. No. 10/948,591.
USPTO Office Action dated Mar. 14, 2007, for copending U.S. Appl. No. 10/455,016.
USPTO Office Action dated May 17, 2007 for copending U.S. Appl. No. 11/201,512.
USPTO Office Action dated Jul. 6, 2007 for copending U.S. Appl. No. 10/455,016.
USPTO office action dated Jul. 19, 2006 for copending U.S. Appl. No. 10/455,017.
USPTO office action dated Jul. 19, 2006 for copending U.S. Appl. No. 10/455,018.
USPTO office action dated Jul. 19, 2006 for copending U.S. Appl. No. 10/455,016.
Treybal, Robert E., "Stagewise Contact, Single-Stage Extraction," Mass-Transfer Operations, Third Edition, 1980, pp. 490-555, McGraw-Hill Book Company.
Notice of Allowance dated Aug. 1, 2007 for copending U.S. Appl. No. 10/975,252.
Notice of Allowance dated Jul. 18, 2007 for copending U.S. Appl. No. 10/975,256.
Copending U.S. Appl. No. 11/839,575, filed Aug. 16, 2007, Philip Edward Gibson et al.
Copending U.S. Appl. No. 11/839,578, filed Aug. 16, 2007, Philip Edward Gibson et al.
Copending U.S. Appl. No. 11/839,582, filed Aug. 16, 2007, Philip Edward Gibson et al.
Copending U.S. Appl. No. 11/839,573, filed Aug. 16, 2007, Kenny Randolph Parker et al.
Copending U.S. Appl. No. 11/842,413, filed Aug. 21, 2007, Kenny Randolph Parker et al.
USPTO Office Action dated Sep. 11, 2007 for copending U.S. Appl. No. 10/455,017.
USPTO Notice of Allowance dated Sep. 11, 2007 for copending U.S. Appl. No. 10/455,018.
USPTO Office Action dated Sep. 25, 2007 for copending U.S. Appl. No. 11/655,396.
USPTO Office Action dated Sep. 25, 2007 for copending U.S. Appl. No. 11/655,395.
USPTO Office Action dated Oct. 16, 2007 for copending U.S. Appl. No. 11/655,317.
BHS—Werk Sonthofen, *BHS-FEST Pressure Filter*, 1990, pamphlet, Santhofen, West Germany.
USPTO Office Action dated Oct. 20, 2004 for U.S. Appl. No. 10/455,017.
USPTO Office Action dated Jun. 6, 2005 for U.S. Appl. No. 10/455,017.
USPTO Office Action dated Nov. 10, 2005 for U.S. Appl. No. 10/455,017.
Copending U.S. Appl. No. 10/156,312, filed May 28, 2002.
Copending U.S. Appl. No. 10/948,591, filed Sep. 24, 2004.
Copending U.S. Appl. No. 10/948,678, filed Sep. 24, 2004.
Copending U.S. Appl. No. 10/975,256, filed Oct. 28, 2004.
Copending U.S. Appl. No. 10/975,252, filed Oct. 28, 2004.
USPTO Notice of Allowance dated Dec. 3, 2007 for copending U.S. Appl. No. 10/455,017.
USPTO Notice of Allowance dated Oct. 1, 2008 for copending U.S. Appl. No. 10/948,591.
USPTO Notice of Allowance dated Oct. 10, 2008 for copending U.S. Appl. No. 11/842,469.
USPTO Office Action dated Mar. 14, 2008 for copending U.S. Appl. No. 10/948,678.
USPTO Office Action dated Mar. 11, 2008 for copending U.S. Appl. No. 11/655,395.
USPTO Office Action dated Mar. 11, 2008 for copending U.S. Appl. No. 11/839,582.
USPTO Office Action dated Mar. 11, 2008 for copending U.S. Appl. No. 11/839,573.
Copending U.S. Appl. No. 12/050,251, filed Mar. 18, 2008, Robert Lin et al.
Copending U.S. Appl. No. 12/050,253, filed Mar. 18, 2008, Robert Lin et al.
Copending U.S. Appl. No. 12/050,256, filed Mar. 18, 2008, Robert Lin et al.
Copending U.S. Appl. No. 12/050,258, filed Mar. 18, 2008, Robert Lin et al.
USPTO Office Action dated Apr. 25, 2008 for copending U.S. Appl. No. 11/181,214.
USPTO Office Action dated Dec. 5, 2008 for copending U.S. Appl. No. 11/655,396.
USPTO Office Action dated Dec. 11, 2008 for copending U.S. Appl. No. 11/839,575.
USPTO Office Action dated Dec. 10, 2008 for copending U.S. Appl. No. 11/839,578.
USPTO Office Action dated Dec. 10, 2008 for copending U.S. Appl. No. 11/839,582.
USPTO Office Action dated Dec. 11, 2008 for copending U.S. Appl. No. 11/839,573.
USPTO Office Action dated Mar. 12, 2009 for copending U.S. Appl. No. 12/050,256.
USPTO Office Action dated Mar. 13, 2009 for copending U.S. Appl. No. 12/050,253.
USPTO Office Action dated Mar. 6, 2009 for copending U.S. Appl. No. 11/655,395.

USPTO Office Action dated Nov. 5, 2008 for copending U.S. Appl. No. 11/201,799.
USPTO Office Action dated Nov. 12, 2008 for copending U.S. Appl. No. 10/948,678.
USPTO Office Action dated Nov. 14, 2008 for copending U.S. Appl. No. 11/655,317.
USPTO Notice of Allowance dated Jun. 11, 2009 for copending U.S. Appl. No. 11/201,799.
USPTO Office Action dated Aug. 19, 2009 for copending U.S. Appl. No. 11/655,317.
USPTO Office Action dated Oct. 14, 2009 for copending U.S. Appl. No. 11/655,396.
USPTO Office Action dated May 21, 2009 for copending U.S. Appl. No. 11/181,214.
USPTO Notice of Allowance dated May 22, 2009 for copending U.S. Appl. No. 12/050,251.
USPTO Office Action dated Aug. 14, 2009 for copending U.S. Appl. No. 11/839,582.
USPTO Office Action dated Aug. 14, 2009 for copending U.S. Appl. No. 11/839,575.
USPTO Office Action dated Sep. 11, 2009 for copending U.S. Appl. No. 11/839,578.
USPTO Office Action dated Aug. 3, 2009 for copending U.S. Appl. No. 11/839,573.
USPTO Office Action dated Dec. 17, 2009 for copending U.S. Appl. No. 11/839,575.
USPTO Office Action dated Jan. 7, 2010 for copending U.S. Appl. No. 12/050,253.
USPTO Office Action dated Apr. 8, 2010 for copending U.S. Appl. No. 11/839,582.
USPTO Office Action dated Apr. 13, 2010 for copending U.S. Appl. No. 11/839,578.
USPTO Notice of Allowance dated May 5, 2010 for copending U.S. Appl. No. 11/839,582.
USPTO Office Action dated Dec. 2, 2009 for copending U.S. Appl. No. 11/655,395.
USPTO Office Action dated Dec. 2, 2009 for copending U.S. Appl. No. 11/839,573.
USPTO Office Action dated Dec. 11, 2009 for copending U.S. Appl. No. 12/050,256.
USPTO Office Action dated Sep. 10, 2010 for copending U.S. Appl. No. 12/050,258.
USPTO Office Action dated Sep. 23, 2010 for copending U.S. Appl. No. 11/839,578.
USPTO Office Action dated Jun. 8, 2010 for copending U.S. Appl. No. 11/655,396.
USPTO Office Action dated Jun. 18, 2010 for copending U.S. Appl. No. 12/050,256.
USPTO Office Action dated Jul. 9, 2010 for copending U.S. Appl. No. 11/839,573.
USPTO Office Action dated Jul. 20, 2010 for copending U.S. Appl. No. 11/655,395.
USPTO Office Action dated Aug. 2, 2010 for copending U.S. Appl. No. 11/839,575.
USPTO Notice of Allowance dated Nov. 8, 2010 for copending U.S. Appl. No. 11/839,573.
USPTO Office Action dated Oct. 18, 2010 for copending U.S. Appl. No. 11/839,575.
USPTO Notice of Allowance dated Nov. 23, 2010 for copending U.S. Appl. No. 11/655,396.
USPTO Notice of Allowance dated Dec. 27, 2010 for copending U.S. Appl. No. 12/050,256.
USPTO Notice of Allowance dated Dec. 16, 2010 for copending U.S. Appl. No. 11/655,395.
USPTO Notice of Allowance dated Dec. 16, 2010 for copending U.S. Appl. No. 11/839,575.

* cited by examiner

OPTIMIZED PRODUCTION OF AROMATIC DICARBOXYLIC ACIDS

RELATED APPLICATIONS

This application claims the priority benefit of U.S. Provisional Pat. App. Ser. No. 60/606,585, filed Sep. 2, 2004, the entire disclosure of which is incorporated herein by reference. This application has been filed concurrently with U.S. application Ser. No. 11/181,214 filed on Jul. 14, 2005, titled "Optimized Production of Aromatic Dicarboxylic Acids", the entire disclosure of which is herein incorporated by reference.

FIELD OF THE INVENTION

This invention relates generally to the production of aromatic dicarboxylic acids, such as terephthalic acid. One aspect of the invention concerns a more efficient method and apparatus for producing aromatic dicarboxylic acids. Another aspect of the invention concerns a method and apparatus for controlling the purity of an aromatic dicarboxylic acid product.

BACKGROUND OF THE INVENTION

Terephthalic acid (TPA) is one of the basic building blocks in the production of linear polyester resins used in the manufacture of polyester films, packaging materials, and bottles. TPA used in the manufacture of such polyesters resins must meet certain minimum purity requirements.

The purified condition of TPA refers primarily to the absence of significant concentrations of 4-carboxybenzaldehyde (4-CBA) and para-toluic acid (p-TAc) that are present in significant quantities in the commercially-available crude grades of TPA. Both 4-CBA and p-TAc are partial oxidation products formed in the manufacture of TPA by the catalytic oxidation of para-xylene. The purified form of TPA also refers to the absence of color bodies that impart a characteristic yellow hue to the crude material. The color bodies are aromatic compounds having the structures of benzils, fluorenones, and/or anthraquinones. 4-CBA and p-TAc are particularly detrimental to the polymerization process as they act as chain terminators during the condensation reaction between TPA and ethylene glycol in the production of polyethylene terephthalate (PET).

In a typical process for producing TPA, a slurry is withdrawn from the primary oxidation reactor. The slurry contains a liquid mother liquor and solid crude terephthalic acid (CTA) particles. The CTA particles are typically separated from the liquid mother liquor and then subjected to purification to thereby produce purified terephthalic acid (PTA). The separated mother liquor is typically treated to remove waste materials and then recycled to the primary oxidation reactor. Although most of the TPA produced in the primary oxidation reactor exists as solid CTA particles, a fraction of the TPA produced in the primary oxidation reactor is present in the liquid mother liquor. In conventional processes, the TPA in the liquid mother liquor represents a potential yield loss if it is not recovered and purified.

One conventional method of purifying CTA to produce PTA is by hydrogenation treatment, where 4-CBA is hydrogenated to p-TAc and color bodies to colorless solid compounds. To accomplish purification by hydrogenation, solid CTA particles are typically dissolved in a solvent (e.g., water), and the resulting solution is subjected to liquid-phase hydrogenation in the presence of a hydrogenation catalyst. Although effective to reduce yellowness, purification of CTA by hydrogenation can be expensive because it consumes energy, hydrogen, water, and catalyst. Hence, from the standpoint of operational cost, it would be desirable to minimize the amount of hydrogenation required to produce TPA solids of suitable purity.

SUMMARY OF THE INVENTION

One embodiment of the present invention concerns a process comprising the following steps: (a) providing a slurry comprising a solid phase and a liquid phase, wherein the solid phase contains a first quantity of terephthalic acid, wherein the liquid phase contains a second quantity of terephthalic acid; (b) subjecting at least a portion of the first quantity of terephthalic acid to oxidation treatment to thereby produce oxidation-treated terephthalic acid; and (c) subjecting at least a portion of the second quantity of terephthalic acid to hydrogenation treatment to thereby produce hydrogenation-treated terephthalic acid.

Another embodiment of the present invention concerns a process comprising the following steps: (a) oxidizing para-xylene in an initial oxidation reactor, thereby producing initial terephthalic acid; (b) subjecting a first portion of the initial terephthalic acid to hydrogenation treatment, thereby producing a hydrogenation-treated terephthalic acid; and (c) combining at least a portion of the hydrogenation-treated terephthalic acid with unhydrogenated terephthalic acid not subjected to the hydrogenation of step (b), wherein the unhydrogenated terephthalic acid originates from a second portion of the initial terephthalic acid.

Still another embodiment of the present invention concerns a process comprising the following steps: (a) introducing a liquid-phase medium into an evaporation zone, wherein the liquid-phase medium comprises a mother liquor and terephthalic acid; (b) evaporating at least a portion of the mother liquor from the liquid-phase medium to thereby form a concentrated medium, wherein the concentrated medium comprises an unevaporated portion of the mother liquor and substantially all of the terephthalic acid; (c) displacing at least a portion of the unevaporated mother liquor with a wash medium, thereby providing a hydrogenation medium comprising the wash medium and the terephthalic acid; and (d) subjecting at least a portion of the hydrogenation medium to hydrogenation treatment, thereby forming a hydrogenation-treated medium.

Yet another embodiment of the present invention concerns an apparatus comprising an initial oxidation reactor, an optional secondary oxidation reactor, a solid/liquid separator, a hydrogenation system, and a combining zone. The initial oxidation reactor has an initial reactor outlet. The optional secondary oxidation reactor has a secondary reactor inlet and a secondary reactor outlet. The secondary reactor inlet is coupled in communication with the initial reactor outlet. The solid/liquid separator has a separator inlet, a separated solids outlet, and a separated liquids outlet. The separator inlet is coupled in communication with the initial reactor outlet and/or the secondary reactor outlet. The hydrogenation system has a hydrogenation system inlet and a hydrogenation system outlet. The hydrogenation system inlet is coupled in communication with the separated liquids outlet. The combining zone has a hydrogenated solids inlet, an unhydrogenated solids inlet, and a composite solids outlet. The hydrogenated solids inlet is coupled in communication with the hydrogenation system outlet and the unhydrogenated solids inlet is coupled in communication with the separated solids outlet.

DETAILED DESCRIPTION

Figure 1:
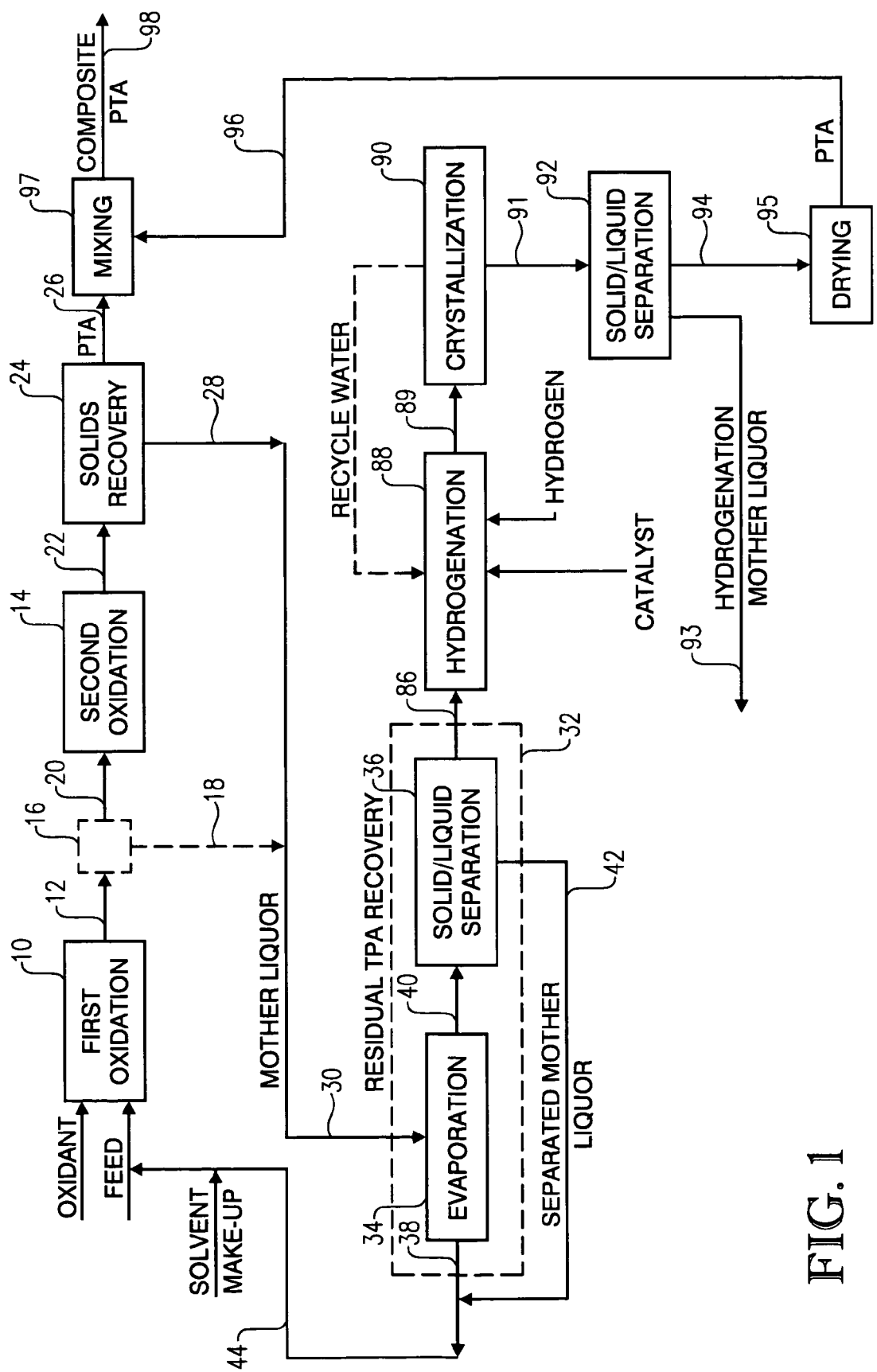
FIG. 1 is a process flow diagram illustrating a system for the production of a terephthalic acid wherein a primary portion of the terephthalic acid is purified by oxidation treatment and a residual portion of the terephthalic acid is purified by hydrogenation treatment.

FIG. 1 illustrates an embodiment of the present invention where terephthalic acid (TPA) produced in a primary/initial oxidation reactor 10 is purified both by oxidation treatment and hydrogenation treatment. In a first step of the embodiment shown in FIG. 1, a predominately liquid-phase feed stream containing an oxidizable compound (e.g., para-xylene), a solvent (e.g., acetic acid+water), and a catalyst system (e.g., Co+Mn+Br) is introduced into primary oxidation reactor 10. A predominately gas-phase oxidant stream containing molecular oxygen is also introduced into primary oxidation reactor 10. The liquid- and gas-phase feed streams form a multi-phase reaction medium in oxidation reactor 10. The oxidizable compound undergoes partial oxidation in a liquid phase of the reaction medium contained in reactor 10.

Primary oxidation reactor 10 is preferably an agitated reactor. Agitation of the reaction medium in oxidation reactor 10 can be provided by any means known in the art. As used herein, the term "agitation" shall denote work dissipated into the reaction medium causing fluid flow and/or mixing. In one embodiment, primary oxidation reactor 10 is a mechanically-agitated reactor equipped with means for mechanically agitating the reaction medium. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. In a preferred embodiment of the invention, primary oxidation reactor 10 is a bubble column reactor. As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the terms "majority," "primarily," and "predominately" shall mean more than 50 percent.

The oxidizable compound present in the liquid-phase feed stream introduced into primary oxidation reactor 10 preferably comprises at least one hydrocarbyl group. More preferably, the oxidizable compound is an aromatic compound. Still more preferably, the oxidizable compound is an aromatic compound with at least one attached hydrocarbyl group or at least one attached substituted hydrocarbyl group or at least one attached heteroatom or at least one attached carboxylic acid function (—COOH). Even more preferably, the oxidizable compound is an aromatic compound with at least one attached hydrocarbyl group or at least one attached substituted hydrocarbyl group with each attached group comprising from 1 to 5 carbon atoms. Yet still more preferably, the oxidizable compound is an aromatic compound having exactly two attached groups with each attached group comprising exactly one carbon atom and consisting of methyl groups and/or substituted methyl groups and/or at most one carboxylic acid group. Even still more preferably, the oxidizable compound is para-xylene, meta-xylene, para-tolualdehyde, meta-tolualdehyde, para-toluic acid, meta-toluic acid, and/or acetaldehyde. Most preferably, the oxidizable compound is para-xylene.

A "hydrocarbyl group," as defined herein, is at least one carbon atom that is bonded only to hydrogen atoms or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. Aromatic compounds, as defined herein, comprise an aromatic ring, preferably having at least 6 carbon atoms, even more preferably having only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the liquid-phase feed stream introduced into primary oxidation reactor 10 is preferably in the range of from about 2 to about 40 weight percent, more preferably in the range of from about 4 to about 20 weight percent, and most preferably in the range of from 6 to 15 weight percent.

The solvent present in the liquid-phase feed stream introduced into primary oxidation reactor 10 preferably comprises an acid component and a water component. The solvent is preferably present in the liquid-phase feed stream at a concentration in the range of from about 60 to about 98 weight percent, more preferably in the range of from about 80 to about 96 weight percent, and most preferably in the range of from 85 to 94 weight percent. The acid component of the solvent is preferably an organic low molecular weight monocarboxylic acid having 1-6 carbon atoms, more preferably 2 carbon atoms. Most preferably, the acid component of the solvent is acetic acid. Preferably, the acid component makes up at least about 75 weight percent of the solvent, more preferably at least about 80 weight percent of the solvent, and most preferably 85 to 98 weight percent of the solvent, with the balance being water.

The liquid-phase feed stream introduced into primary oxidation reactor 10 can also include a catalyst system. The catalyst system is preferably a homogeneous, liquid-phase catalyst system capable of promoting partial oxidation of the oxidizable compound. More preferably, the catalyst system comprises at least one multivalent transition metal. Still more preferably, the multivalent transition metal comprises cobalt. Even more preferably, the catalyst system comprises cobalt and bromine. Most preferably, the catalyst system comprises cobalt, bromine, and manganese.

When cobalt is present in the catalyst system, it is preferred for the amount of cobalt present in the liquid-phase feed stream to be such that the concentration of cobalt in the liquid phase of the reaction medium is maintained in the range of from about 300 to about 6,000 parts per million by weight (ppmw), more preferably in the range of from about 700 to about 4,200 ppmw, and most preferably in the range of from 1,200 to 3,000 ppmw. When bromine is present in the catalyst system, it is preferred for the amount of bromine present in the liquid-phase feed stream to be such that the concentration of bromine in the liquid phase of the reaction medium is maintained in the range of from about 300 to about 5,000 ppmw, more preferably in the range of from about 600 to about 4,000 ppmw, and most preferably in the range of from 900 to 3,000 ppmw. When manganese is present in the catalyst system, it is preferred for the amount of manganese present in the liquid-phase feed stream to be such that the concentration of manganese in the liquid phase of the reaction medium is maintained in the range of from about 20 to about 1,000 ppmw, more preferably in the range of from about 40 to about 500 ppmw, most preferably in the range of from 50 to 200 ppmw.

The weight ratio of cobalt to bromine (Co:Br) in the catalyst system introduced into primary oxidation reactor 10 is preferably in the range of from about 0.25:1 to about 4:1, more preferably in the range of from about 0.5:1 to about 3:1, and most preferably in the range of from 0.75:1 to 2:1. The weight ratio of cobalt to manganese (Co:Mn) in the catalyst system introduced is preferably in the range of from about 0.3:1 to about 40:1, more preferably in the range of from about 5:1 to about 30:1, and most preferably in the range of from 10:1 to 25:1.

During oxidation, it is preferred for the oxidizable compound (e.g., para-xylene) to be continuously introduced into primary oxidation reactor 10 at a rate of at least about 5,000 kilograms per hour, more preferably at a rate in the range of from about 10,000 to about 80,000 kilograms per hour, and most preferably in the range of from 20,000 to 50,000 kilograms per hour. During oxidation, it is preferred for the ratio of the mass flow rate of the solvent to the mass flow rate of the oxidizable compound entering oxidation reactor 10 to be maintained in the range of from about 2:1 to about 50:1, more preferably in the range of from about 5:1 to about 40:1, and most preferably in the range of from 7.5:1 to 25:1.

The predominately gas-phase oxidant stream introduced into primary oxidation reactor 10 preferably comprises in the range of from about 5 to about 40 mole percent molecular oxygen, more preferably in the range of from about 15 to about 30 mole percent molecular oxygen, and most preferably in the range of from 18 to 24 mole percent molecular oxygen. It is preferred for the balance of the oxidant stream to be comprised primarily of a gas or gases, such as nitrogen, that are inert to oxidation. More preferably, the oxidant stream consists essentially of molecular oxygen and nitrogen. Most preferably, the oxidant stream is dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in primary oxidation reactor 10, it is preferred for the oxidant stream to be introduced into reactor 10 in an amount that provides molecular oxygen somewhat exceeding the stoichiometric oxygen demand. Thus, it is preferred that the ratio of the mass flow rate of the oxidant stream (e.g., air) to the mass flow rate of the oxidizable compound (e.g., para-xylene) entering reactor 10 is maintained in the range of from about 0.5:1 to about 20:1, more preferably in the range of from about 1:1 to about 10:1, and most preferably in the range of from 2:1 to 6:1.

The liquid-phase oxidation reaction carried out in reactor 10 is preferably a precipitating reaction that generates solids. More preferably, the liquid-phase oxidation carried out in reactor 10 causes at least about 10 weight percent of the oxidizable compound (e.g., para-xylene) introduced into oxidation reactor 10 to form solids (e.g., CTA particles) in the reaction medium. Still more preferably, the liquid-phase oxidation causes at least about 50 weight percent of the oxidizable compound to form solids in the reaction medium. Most preferably, the liquid-phase oxidation causes at least 90 weight percent of the oxidizable compound to form solids in the reaction medium. It is preferred that the total amount of solids in the reaction medium is maintained in the range of from about 5 to about 40 weight percent, still more preferably in the range of from about 10 to about 35 weight percent, and most preferably in the range of from 15 to 30 weight percent.

During oxidation in oxidation reactor 10, the multi-phase reaction medium is preferably maintained at an elevated temperature in the range of from about 125 to about 225° C., more preferably in the range of from about 150 to about 180° C., and most preferably in the range of from 155 to 165° C. The overhead pressure in oxidation reactor 10 is preferably maintained in the range of from about 1 to about 20 bar atmospheric (bara), more preferably in the range of from about 3.5 to about 13 bara, and most preferably in the range of from 5.2 to 6.9 bara.

As illustrated in FIG. 1, a crude product slurry is withdrawn from an outlet of primary oxidation reactor 10 via line 12. The solid phase of the crude product slurry in line 12 is formed primarily of solid particles of crude terephthalic acid (CTA). The liquid phase of the crude product slurry in line 12 is a liquid mother liquor comprising at least a portion of the solvent, the catalyst system, and minor amounts of dissolved TPA. The amount of TPA present in the mother liquor is preferably less than about 10 weight percent of the total TPA present in the crude product slurry exiting primary oxidation reactor 10, more preferably the range of from about 0.1 to about 5 weight percent of the total TPA, and most preferably in the range of from 0.5 to 3 weight percent of the total TPA. The solids content of the crude product slurry in line 12 is preferably the same as the solids content of the reaction medium in primary oxidation reactor 10, discussed above.

In one embodiment of the present invention, the crude product slurry in line 12 is transported directly to a secondary oxidation reactor 14 for purification by oxidation treatment. In an alternative embodiment, an optional liquor removal system 16 is employed to remove at least a portion of the liquid mother liquor from the crude product slurry prior introduction into secondary oxidation reactor 14. Liquor removal system 16 can employ a variety of different apparatuses to remove/separate at least a portion of the mother liquor from the crude product slurry in line 12. For example, liquor removal system 16 can be a liquor exchange system that separates at least a portion of the mother liquor from the crude product slurry and then uses a clean replacement solvent to replace at least a portion of the removed mother liquor. Separation of the mother liquor from the solid in liquor removal system 16 can be accomplished using an suitable solid/liquid separator such as, for example, a decanter centrifuge, a rotary disk centrifuge, a belt filter, or a rotary vacuum filter. When liquor removal system 16 is employed, the removed mother liquor is passed through line 18 for further processing (described in detail below), while the resulting crude product slurry is passed through line 20 to secondary oxidation reactor 14.

In secondary oxidation reactor 14, the crude product slurry is subjected to purification by oxidation treatment. Secondary oxidation reactor 14 is preferably an agitated reactor, most preferably a mechanically-agitated reactor. A secondary oxidant stream is provided to secondary oxidation reactor 14 to provide the molecular oxygen required for secondary oxidation. Additional catalyst can also be added if necessary. The crude product slurry introduced into secondary oxidation reactor 14 contains significant quantities of impurities such as, for example, 4-carboxybenzaldehyde (4-CBA) and para-toluic acid (p-TAc). The oxidation treatment in secondary oxidation reactor 14 preferably causes oxidation of a substantial portion of the 4-CBA and p-TAc to TPA.

The temperature at which oxidation is carried out in secondary oxidation reactor 14 is preferably at least about 10° C. greater than the temperature of oxidation in primary oxidation reactor 10, more preferably in the range of from about 20 to about 80° C. greater, and most preferably in the range of from 30 to 50° C. greater. The additional heat required for the operation of secondary oxidation reactor 14 may be provided by supplying a vaporized solvent to secondary oxidation reactor and allowing the vaporized solvent to condense therein. The oxidation temperature in secondary oxidation reactor is preferably maintained in the range of from about 175 to about 250° C., more preferably in the range of from about 185 to about 230° C., and most preferably in the range of from 195 to 210° C. The oxidation pressure in secondary oxidation reactor 14 is preferably maintained in the range of from about 2 to about 30 bara, more preferably in the range of from about 4.5 to about 18.3 bara, and most preferably in the range of from 13.4 to 17.2 bara.

An oxidation-treated slurry is discharged from secondary oxidation reactor 14 via line 22. The solid phase of the oxidation-treated slurry is formed primarily of purified terephthalic acid (PTA) particles, while the liquid phase is formed of an oxidation-treated mother liquor. The solids content of the oxidation-treated slurry in line 22 is preferably in the same ranges disclosed above for the solids content of the crude product slurry in line 12.

The oxidation-treated slurry in line 22 is transported to a solids recovery system 24 for removal of the oxidation-treated mother liquor and recovery of solid PTA particles. Solids recovery system preferably includes at least one solid/liquid separator and at least one drier. The solid/liquid separator employed as part of solids recovery system 24 can be any conventional solid/liquid separator such as, for example, a decanter centrifuge, a rotary disk centrifuge, a belt filter, or a rotary vacuum filter. The solids separated in the solid/liquid separator can then be dried using any suitable drier known in the art. The recovered, dried PTA solids are discharged from solids recovery system 24 via line 26. The separated oxidation-treated mother liquor is discharged from solids recovery system 24 via line 28.

The separated mother liquor in line 28 can be combined with the optional separated mother liquor in line 18, if present. The combined mother liquor stream in line 30, which contains a small amount of residual TPA, can then be directed to a residual TPA recovery system 32. Residual TPA recovery preferably includes at least one evaporator 34 and a solid/liquid separator 36. Evaporator 34 is operable to remove a substantial portion of the solvent (e.g., acetic acid and water) from the mother liquor. The evaporated solvent is discharged from evaporator 34 via line 38. Preferably, evaporator 34 includes a first evaporator zone operated at or above atmospheric pressure (e.g., 1-10 atmospheres) and a second evaporator zone operated at vacuum conditions. The second evaporation zone is preferably maintained at a temperature in the range of from about 10 to about 100° C., more preferably in the range of from about 20 to about 70° C., and most preferably in the range of from 30 to 50° C. It is preferred for at least about 25 weight percent of the mother liquor introduced into evaporator 34 to be evaporated and discharge via line 38, more preferably at least about 50 weight percent of the mother liquor introduced into evaporator 34 is evaporated and discharged via line 38, and most preferably in the range of from 75 to 99 weight percent of the mother liquor introduced into evaporator 34 is evaporated and discharged via line 38.

A concentrated slurry is discharged from evaporator 34 via line 40. The concentrated slurry in line 40 preferably contains more than about 10 weight percent solid TPA particles and less than 90 weight percent liquids. The concentrated slurry in line 40 preferably contains less than about 10 weight percent of the total TPA discharged from primary oxidation reactor via line 12, more preferably in the range of from about 0.1 to about 5 weight percent of the total TPA from reactor 10, and most preferably in the range of from 0.5 to 3 weight percent of the total TPA from reactor 10.

The concentrated slurry in line 40 is introduced into solid/liquid separator 36 where substantially all of the remaining liquid mother liquor is removed from the concentrated slurry. The removed mother liquor is discharged from solid/liquid separator 36 via line 42 and subsequently combined with the evaporated mother liquor in line 38. The combined mother liquor in line 44 can then be recycled to primary oxidation reactor 10 via combination with the liquid-phase feed stream introduced into reactor 10, although a portion of all of the combined mother liquor can be removed from the process.

Figure 2:
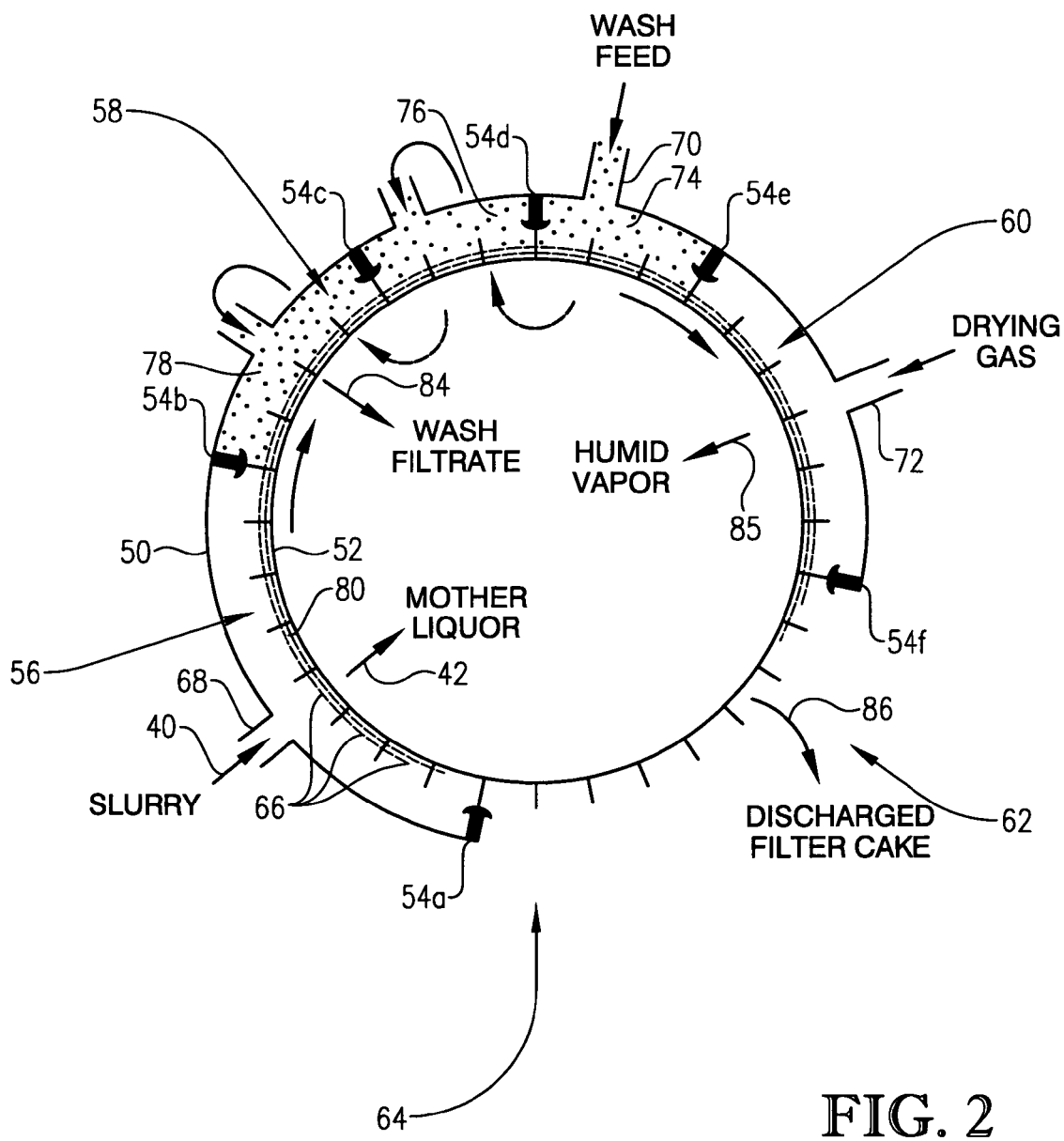
FIG. 2 is a schematic representation of a pressure filter that can be employed to help recover residual terephthalic acid from liquid mother liquor produced by one or more oxidation reactors.

Solid/liquid separator 36 preferably employs a rotary drum pressure filter device similar to the device illustrated in FIG. 2. The rotary drum pressure filter of FIG. 2 comprises a housing 50 and a rotary drum filter 52 rotatably disposed within housing 50. An annulus is defined between the inside of housing 50 and the outside of rotary drum filter 52. This annulus is divided into various discreet zones by seals 54a,b, c,d,e,f. A filtration zone 56 is defined in the annulus between seals 54a and 54b. A wash zone 58 is defined in the annulus between seals 54b and 54e. A drying/dewatering zone 60 is defined in the annulus between seals 54e and 54f. Housing 50 is open between seals 54f and 54a. This open portion of housing 50 includes a discharge zone 62 and a cloth wash zone 64.

Referring again to FIG. 2, rotary drum filter 52 defines a plurality of filter cells 66 located on the periphery of the drum. The bottom of each filter cell 66 is formed of a filter media (e.g., synthetic cloth, single-layer metal, or multi-layer metal). Fluid flow through the filter media is caused by creating a pressure differential across the filter media. Each filter cell 66 has its own outlet for discharging fluids inwardly towards the axis of rotation of rotary drum filter 52. The outlets of axially-aligned filter cells 66 are manifolded. The manifolds (not shown) rotate with the rotary drum filter 52 and communicate with a service/control head (not shown) which collects the fluids from the manifolds in a manner that allows the fluids discharged from zones 56,58,60 to be kept separate.

Housing 50 defines a concentrated slurry inlet 68 that communicates with filtration zone 56, a wash feed inlet 70 that communicates with wash zone 58, and a drying gas inlet 72 that communicates with drying/dewatering zone 60. Wash zone 58 is divided into an initial wash zone 74, an intermediate wash zone 76, and a final wash zone 78 by seals 54c and 54d. Housing 50 and rotary drum filter 52 are configured to permit filtrate discharged from initial wash zone 74 to enter intermediate wash zone 76, and filtrate discharge from intermediate wash zone 76 to enter final wash zone 78.

In operation, the concentrated slurry in line 40 enters filtration zone 56 via slurry inlet 68 and forms a filter cake 80 in filter cells 66 on the periphery of rotary filter drum 52. In filtration zone 56, liquid mother liquor is discharged radially inward from the bottom of each filter cell 66. The mother liquor collected from filtration zone 56 can be discharged from the apparatus via line 42. Upon obtaining a preferred height of filter cake 80 in filtration zone 56, rotary drum filter 52 rotates so that filter cake 80 enters wash zone 58.

In wash zone 58, filter cake 80 is washed with a wash feed entering initial wash zone 74 via wash feed inlet 70. The wash feed is preferably formed primarily of water. Most preferably the wash feed consists essentially of water. The wash filtrate from initial wash zone 74 is then transferred to intermediate wash zone 76, and the wash filtrate from intermediate wash zone 76 is transferred to final wash zone 78. The wash filtrate can then be discharged from the apparatus via line 84. In one embodiment of the present invention, the wash filtrate in line 84 is combined into the filtered mother liquor in line 42. After suitable washing in wash zone 58, rotary drum filter 52 rotates so that filter cake 80 enters drying/dewatering zone 60.

In drying/dewatering zone 60, liquid is removed from washed filter cake 80 by passing a drying gas, entering via gas inlet 72, through washed filter cake 80. The gas stream passed through washed filter cake 80 exits the apparatus as a humid vapor via line 85. After filter cake 80 is dried/dewatered in zone 60, rotary drum filter 52 rotates so that dried filter cake 80 enters discharge zone 62.

In discharge zone 62, filter cake 80 is disengaged from rotary drum filter 52 and exits the apparatus via line 86. Rotary filter drum 52 then rotates into cloth wash zone 64 where any solid particles remaining in filter cells 66 are removed.

A suitable pressure filter which can be employed as the solid/liquid separator 36 is a BHS-FEST™, available from BHS-WERK, Sonthofen, D-8972, Sonthofen, West Germany. However, other pressure filters known in the art may be capable of performing the functions required by solid/liquid separator 36 of FIG. 1. Examples of other suitable devices include, for example, belt filters, filter presses, centrifuges, pressure leaf filters, and cross-flow filters. In one embodiment of the present invention, solid/liquid separator has substantially the same configuration and operating parameters as the pressure filter described in U.S. patent application Ser. No. 10/874,419, filed Jun. 23, 2004, the entire disclosure of which is incorporated by reference herein.

Referring again to FIG. 1, the solids exiting solid/liquid separator 36 via conduit 86 are preferably residual TPA solids that originate from the liquid phase of the slurry exiting primary oxidation reactor 10 and/or secondary oxidation reactor 14. These residual TPA particles in line 86 are subjected to purification by hydrogenation treatment in a hydrogenation system 88. Hydrogenation system 88 can include one or more vessels/zones. Preferably, hydrogenation system 88 includes an initial dissolution zone/vessel where the residual TPA solids are combined with a solvent (preferably water) at an elevated temperature to thereby cause dissolution of the residual TPA solids in the solvent. The solvent and residual TPA particles are preferably combined at a solvent-to-TPA weight ratio in the range of from about 0.5:1 to about 50:1, more preferably in the range of from about 1:1 to about 10:1, and most preferably in the range of from 1.5:1 to 5:1.

After dissolution of the residual TPA particles in the solvent, the resulting solution is introduced into a hydrogenation zone/vessel of hydrogenation system 88 where the solution is contacted with hydrogen and a hydrogenation catalyst under conditions sufficient to cause hydrogenation of certain impurities present therein (e.g., hydrogenation of 4-CBA to p-TAc and/or floureneones to flourenes). In a preferred embodiment of the invention, hydrogenation treatment is carried out at a temperature in the range of from about 200 to about 400° C., more preferably in the range of from about 250 to about 350° C., and most preferably in the range of from about 260 to 320° C. The pressure in the hydrogenation zone/vessel is preferably maintained in the range of from about 5 to about 200 bara, more preferably in the range of from about 10 to about 150 bara, and most preferably in the range of from 46.9 to 113 bara. The average space velocity for hydrogenation is preferably maintained in the range of from about 150 to about 2,500 kilograms of solution per hour per cubic meter of catalyst bed (kg/hr/m$^3$), more preferably in the range of from about 300 to about 1,500 kg/hr/m$^3$, and most preferably in the range of from 450 to 850 kg/hr/m$^3$. The molar ratio of hydrogen fed to the hydrogenation zone/vessel to residual TPA fed to the hydrogenation zone/vessel is preferably in the range of from about 5:1 to about 500:1, more preferably in the range of from about 10:1 to about 300:1, and most preferably in the range of from 20:1 to 250:1. The hydrogenation catalyst employed in the hydrogenation zone/vessel is preferably a noble Group VIII metal on a conventional catalyst support material.

After hydrogenation treatment in hydrogenation system 88, the resulting hydrogenation-treated solution is transported in line 89 to a crystallization system 90 where it is subjected to crystallization in at least one crystallizer. In crystallization system 90, the temperature of the hydrogenated solution is lowered to a crystallization temperature in the range of from about 100 to about 200° C., more preferably in the range of from about 120 to about 185° C., and most preferably in the range of from 140 to 175° C. The decreased temperature in crystallization system 90 causes substantially all of the TPA dissolved in the hydrogenation-treated solution to crystallize, thereby forming solid particles of a purified/hydrogenated terephthalic acid (i.e., PTA).

The two-phase (slurry) effluent from crystallization system 90 is transported in line 91 to a solid/liquid separator 92 for separation of the solid and liquid fractions. The separated liquid fraction (i.e., hydrogenation mother liquor) is transported in line 93 for further processing. The separated solid PTA from separator 92 is transported in line 94 for drying in one or more conventional driers 95. The resulting dried hydrogenation-treated PTA particles are transported in line 96 to a combining zone 97 where at least a portion of the hydrogenation-treated PTA particles from line 96 are combined with at least a portion of the oxidation-treated PTA from line 26.

A composite PTA containing oxidation- and hydrogenation-treated PTA is produced from combining zone 97 via line 98. The weight ratio of oxidation-treated PTA to hydrogenation-treated PTA in the composite PTA produced from combining zone 97 is preferably in the range of from about 10:1 to about 1,000:1, more preferably in the range of from about 20:1 to about 500:1, and most preferably in the range of from 50:1 to 250:1. In one embodiment of the present invention, substantially all of the TPA present in the solid phase of the slurry exiting secondary oxidation reactor 14 via line 22 is subsequently introduced into combining zone 97, while substantially all of the TPA present in the hydrogenation-treated solution exiting hydrogenation system 88 via line 89 is also subsequently introduced into combining zone 97. In such an embodiment, the weight ratio of oxidation-treated PTA particles exiting secondary oxidation reactor 14 to hydrogenation-treated PTA exiting hydrogenation system 88 is the same as the weight ratio of oxidation-treated PTA to hydrogenation-treated PTA recited above for the final composite PTA product.

Figure 3:
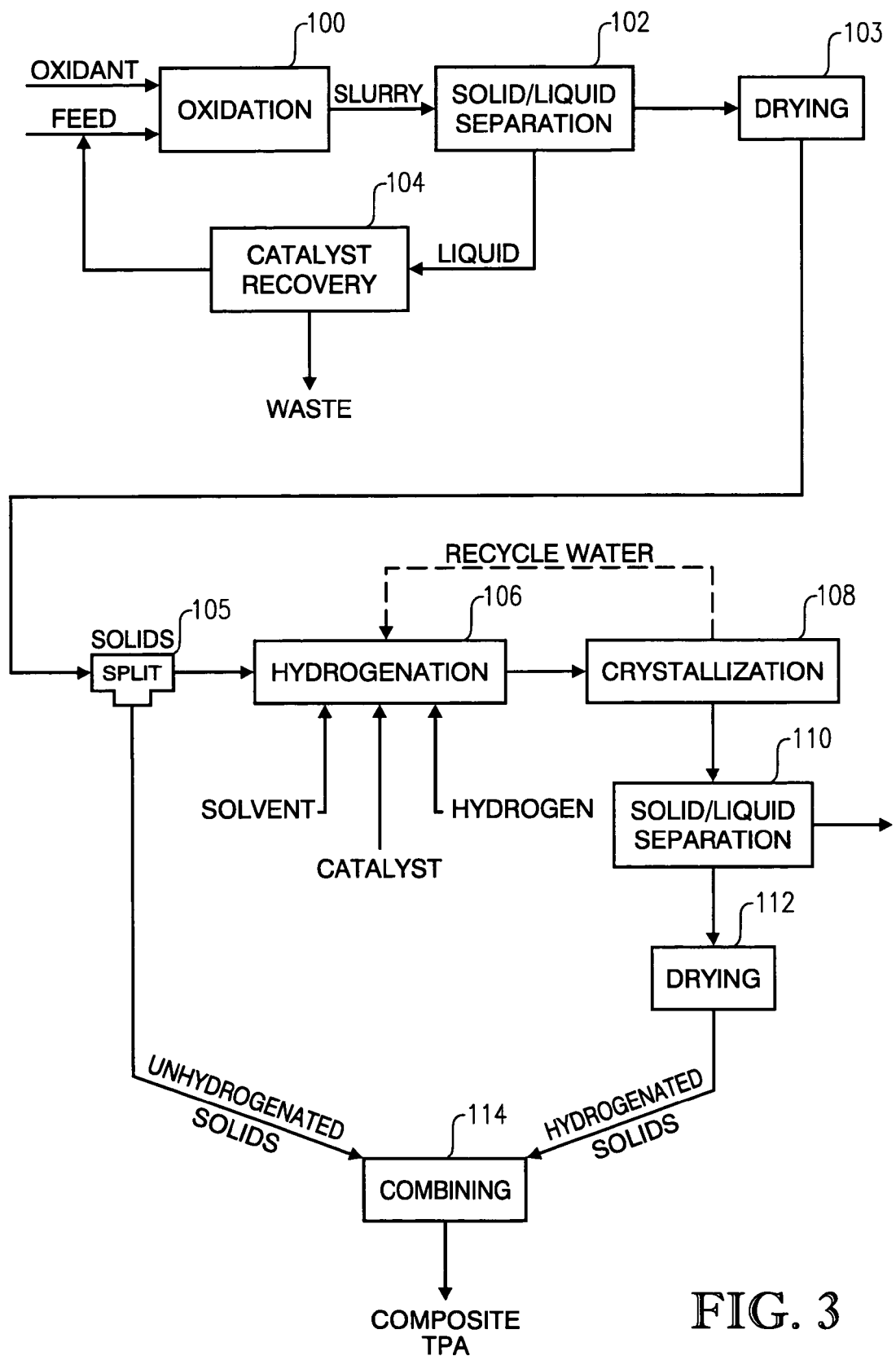
FIG. 3 is a process flow diagram illustrating a system for the production of a composite terephthalic acid that is formed by combining a quantity of purified/hydrogenated terephthalic acid with a quantity of crude/unhydrogenated terephthalic acid.

FIG. 3 illustrates an embodiment of the present invention where a first portion of an initial TPA produced in an oxidation reactor 100 is subjected to hydrogenation treatment, a second portion of the TPA produced in oxidation reactor 100 is not subjected to hydrogenation treatment, and a composite TPA product is formed by combining hydrogenation-treated TPA (originating from the first portion of the initial TPA) and unhydrogenated TPA (originating from the second portion of the TPA).

As shown in FIG. 3, in a first step of the process, a predominately liquid-phase feed stream containing an oxidizable compound (e.g., para-xylene), a solvent (e.g., acetic acid+water), and a catalyst system (e.g., Co+Mn+Br) is introduced into an oxidation reactor 100. A predominately gas-phase oxidant stream containing molecular oxygen is also introduced into reactor 100. The liquid- and gas-phase feed streams form a multi-phase reaction medium in reactor 100. The oxidizable compound undergoes partial oxidation in a liquid phase of the reaction medium contained in reactor 100.

Oxidation reactor 100 is preferably an agitated reactor. Agitation of the reaction medium in oxidation reactor 100 can be provided by any means known in the art. In a preferred embodiment of the present invention, oxidation reactor 100 is a mechanically-agitated reactor (e.g., continuous stirred tank reactor) equipped with means for mechanically agitating the reaction medium. In an alternative embodiment of the invention, oxidation reactor 100 is a bubble column reactor.

The liquid-phase feed stream and gas-phase oxidant stream introduced into oxidation reactor 100 of FIG. 3 are preferably substantially the same as the liquid-phase feed stream and gas-phase feed stream introduced into primary oxidation reactor 10 of FIG. 1. In addition, oxidation reactor 100 of FIG. 3 is preferably operated in substantially the same manner as described above with reference to primary oxidation reactor 10 of FIG. 1. However, when oxidation reactor 100 of FIG. 3 is a mechanically agitated reactor, it is preferred for the multi-phase reaction medium in oxidation reactor 100 to be maintained at an elevated temperature in the range of from about 150 to about 300° C., more preferably in the range of from about 175 to about 250° C., and most preferably in the range of from 190 to 225° C. The overhead pressure in oxidation reactor 100 is preferably maintained in the range of from about 1 to about 20 bar gauge (barg), more preferably in the range of from about 2 to about 12 barg, and most preferably in the range of from 4 to 8 barg.

As illustrated in FIG. 3, a slurry containing solid particles of the crude oxidation product (e.g., CTA) is withdrawn from an outlet of oxidation reactor 100. The solids content of the withdrawn slurry is preferably in the range of from about 5 to about 40 weight percent, still more preferably in the range of from about 10 to about 35 weight percent, and most preferably in the range of from 15 to 30 weight percent. The withdrawn slurry from reactor 100 is introduced into a solid/liquid separator 102 where the slurry is subjected to solid/liquid separation. Separator 102 can be any conventional solid/liquid separation means including, for example, a decanter centrifuge, a rotary disk centrifuge, a belt filter, or a rotary vacuum filter.

The liquid mother liquor discharged through a liquids outlet of solid/liquid separator 102 is introduced into a catalyst recovery system 104. The liquid mother liquor is typically comprised mostly of the solvent and the catalyst system; however, the mother liquor may also contain undesirable corrosion/tramp metals such as iron, nickel and chromium, as well as undesired organic reaction products which have built up over time. Catalyst recovery system 104 employs a conventional method to remove a substantial portion of the undesirable components present in the liquid mother liquor. As illustrated in FIG. 3, the resulting cleaned liquid stream can be combined with the liquid-phase feed stream introduced into oxidation reactor 100.

The crude acid solids (e.g., CTA) discharged through a solids outlet of solid/liquid separator 102 typically is in the form of a solvent wet cake. Optionally, one or more dryers 103 can be utilized to evaporate residual solvent. The CTA typically has a 4-CBA content greater than about 600 parts per million by weight (ppmw). More typically, the 4-CBA content of the crude acid solids is in the range of from about 700 to about 10,000 ppmw, and most typically in the range of from 800 to 7,000 ppmw. Typically, the crude acid solids have a p-TAc content greater than about 150 ppmw. More typically, the p-TAc content of the crude acid solids is in the range of from about 175 to about 5,000 ppmw, and most typically in the range of from 200 to 1,500 ppmw. Typically, the crude acid solids have a combined 4-CBA plus p-TAc content greater than about 700 ppmw. More typically, the combined 4-CBA and p-TAc content of the crude acid solids is in the range of from about 850 to about 10,000 ppmw, and most typically in the range of from 1,000 to 5,000 ppmw. Typically, the crude acid solids have a B* value of at least 3, more typically in the range of from about 3.5 to about 10, and most typically 4 to 8.

Referring again to FIG. 3, the crude acid solids (e.g., CTA) discharged from solid/liquid separator 102 (or, optionally, dryer 103) are introduced into a splitter 105 where the solids are divided into a first portion and a second portion. Splitter 105 can be any conventional means for separating solids. The first portion of the crude acid solids exits a first outlet of splitter 105 and is subsequently subjected to purification in a hydrogenation system 106. The second portion of the crude acid solids exits a second outlet of splitter 105 and is not subject to hydrogenation treatment. It is preferred for at least about 1 weight percent of the crude acid solids (e.g., CTA) produced in oxidation reactor 100 to exit the second outlet of splitter 105 and not be subjected to hydrogenation treatment, more preferably in the range of from about 3 to about 60 weight percent of the crude acid solids are not subjected to hydrogenation treatment, and most preferably in the range of from 5 to about 40 weight percent of the crude acid solids are not subjected to hydrogenation treatment. In addition, is preferred for the weight ratio of to the second portion of the crude acid solids (not subjected to hydrogenation) to the first portion of the crude acid solids (subsequently subjected to hydrogenation) to be in the range of from about 0.01:1 to about 4:1, more preferably in the range of from about 0.05:1 to about 2:1, and most preferably in the range of from 0.1:1 to 1:1.

Hydrogenation system 106 receives the first portion of the crude acid solids from splitter 105. Hydrogenation system 106 can include one or more vessels/zones. Preferably, hydrogenation system 106 includes an initial dissolution zone/vessel where the crude acid solids (e.g., CTA) are combined with a solvent (preferably water) at an elevated temperature to thereby cause dissolution of the crude acid solids in the solvent. The solvent and crude acid particles are preferably combined at a solvent-to-crude acid weight ratio in the range of from about 0.5:1 to about 50:1, more preferably in the range of from about 1:1 to about 10:1, and most preferably in the range of from 1.5:1 to 5:1.

After dissolution of the crude acid particles in the solvent, the resulting solution is introduced into a hydrogenation zone/vessel of hydrogenation system 106 where the solution is contacted with hydrogen and a hydrogenation catalyst under conditions sufficient to cause hydrogenation of certain impurities present therein (e.g., hydrogenation of 4-CBA to p-TAc and/or floureneones to flourenes). In a preferred embodiment of the invention, hydrogenation treatment is carried out at a temperature in the range of from about 200 to about 375° C., more preferably in the range of from about 225 to about 300° C., and most preferably in the range of from 240 to 280° C. The pressure in the hydrogenation zone/vessel is preferably maintained in the range of from about 2 to about 50 barg. The average space velocity for hydrogenation is preferably maintained in the range of from about 150 to about 2,500 kilograms of solution per hour per cubic meter of catalyst bed (kg/hr/m$^3$), more preferably in the range of from about 300 to about 1,500 kg/hr/m$^3$, and most preferably in the range of from 450 to 850 kg/hr/m$^3$. The molar ratio of hydrogen fed to the hydrogenation zone/vessel to crude acid fed to the hydrogenation zone/vessel is preferably in the range of from about 5:1 to about 500:1, more preferably in the range of from about 10:1 to about 300:1, and most preferably in the range of from 20:1 to 250:1. The hydrogenation catalyst employed in the hydrogenation zone/vessel is preferably a noble Group VIII metal on a conventional catalyst support material.

After hydrogenation treatment in hydrogenation system 106, the resulting hydrogenation-treated solution is subjected to crystallization in a crystallization system 108 comprising at least one crystallizer. In crystallization system 108, the temperature of the hydrogenated solution is lowered to a crystallization temperature in the range of from about 100 to about 200° C., more preferably in the range of from about 120 to about 185° C., and most preferably in the range of from 140 to 175° C. The decreased temperature in crystallization system 108 causes substantially all of the aromatic dicarboxylic acid (e.g., TPA) dissolved in the hydrogenation-treated solution to crystallize, thereby forming solid particles of a purified/hydrogenated acid (e.g., PTA).

The two-phase (slurry) effluent from crystallization system 108 is thereafter subjected to solid/liquid separation in a conventional separator 110. The separated purified/hydrogenated acid solids (e.g., PTA) from separator 110 are then dried in one or more conventional driers 112.

The purified/hydrogenated acid solids (e.g., PTA) discharged from drier 112 preferably have a 4-CBA content less than or equal to about 100 ppmw, more preferably less than about 50 ppmw, and most preferably less than 25 ppmw. The purified acid solids preferably have a p-TAc content that is less than about 500 ppmw, more preferably less than about 250 ppmw, and most preferably less than 125 ppmw. The purified acid solids preferably have a combined 4-CBA plus p-TAc content that is less than about 700 ppmw, more preferably less than about 500 ppmw, and most preferably less than 300 ppmw. The purified acid solids preferably have a B* value of less that about 3.0, more preferably less than about 2.0, and most preferably less than 1.5.

The purified/hydrogenated acid solids (e.g., PTA) discharged from drier 112 preferably have a 4-CBA content that is less than 80 percent by weight of the 4-CBA content of the crude/unhydrogenated acid solids (e.g., CTA) discharged from separator 102, more preferably in the range of from about 5 to about 60 percent by weight less 4-CBA, and most preferably in the range of from 10 to 40 percent by weight less 4-CBA. The purified acid solids preferably have a combined 4-CBA plus p-TAc content that is less than 80 percent by weight of the combined 4-CBA plus p-TAc content of the crude acid solids, more preferably in the range of from about 5 to about 60 percent by weight, and most preferably in the range of from 10 to 40 percent by weight. The purified acid solids preferably have a B* value that is less than 80 percent of the B* value the crude acid solids, more preferably in the range of from about 5 to about 60 percent, and most preferably in the range of from 10 to 40 percent.

As illustrated in FIG. 3, at least a portion of purified/hydrogenated acid solids (e.g., PTA) exiting drier 112 are combined in a combining zone/vessel 114 with at least a portion of the crude/unhydrogenated acid solids (e.g., CTA) discharged from splitter 105. A well-mixed composite acid (e.g., composite TPA) comprising the solid purified/hydrogenated acid particles and solid crude/unhydrogenated acid particles is produced in, and discharged from, mixing zone/vessel 114. The combining zone/vessel 114 can be any zone or vessel having an inlet for receiving the purified/hydrogenated acid, an inlet for receiving the crude/unhydrogenated acid, and an outlet for discharging the composite acid. In one embodiment, mixing zone/vessel 114 is equipped with a stirrer to ensure that the resulting composite acid is well-mixed. The composite acid is just pure enough to meet product specifications, but not unnecessarily pure. Since not all of the acid of the final product has been subjected to hydrogenation treatment, various costs associated with hydrogenation are reduced, as compared to processes where all of the final acid product is previously subjected to hydrogenation treatment.

The specific amounts of purified/hydrogenated acid particles and crude/unhydrogenated acid particles combined in mixing zone/vessel 114 varies based on the level of impurities in the purified and crude acid particles, as well as the level of impurities permitted by the final product specifications. In a preferred embodiment of the present invention, the weight ratio of crude/unhydrogenated acid particles to purified/hydrogenated acid particles in the composite acid is in the range of from about 0.01:1 to about 4:1, more preferably in the range of from about 0.05:1 to about 2:1, and most preferably in the range of from about 0.1:1 to about 1:1.

The final composite acid (e.g., composite TPA) product exiting mixing zone/vessel 114 preferably has a 4-CBA content that is at least about 105 percent by weight of the 4-CBA content of the purified/hydrogenated acid (e.g., PTA) exiting drier 112, more preferably in the range of from about 110 to about 400 percent by weight, and most preferably in the range of from about 120 to about 200 percent by weight. The composite acid product preferably has a p-TAc content that is at least about 105 percent by weight of the p-TAc content of the purified/hydrogenated acid, more preferably in the range of from about 110 to about 400 percent by weight, and most preferably in the range of from about 120 to about 200 percent by weight. The composite acid product preferably has a combined 4-CBA plus p-TAc content that is at least about 105 percent by weight of the combined 4-CBA plus p-TAc content of the purified/hydrogenated acid, more preferably in the range of from about 110 to about 400 percent by weight, and most preferably in the range of from about 120 to about 200 percent by weight. The composite acid product preferably has a B* value that is at least about 105 percent of the B* value of the purified/hydrogenated acid, more preferably in the range of from about 110 to about 400, and most preferably in the range of from about 120 to about 200.

The inventors note that for all numerical ranges provided herein, the upper and lower ends of the ranges can be independent of one another. For example, a numerical range of 10 to 100 means greater than 10 and/or less than 100. Thus, a range of 10 to 100 provides support for a claim limitation of greater than 10 (without the upper bound), a claim limitation of less than 100 (without the lower bound), as well as the full 10 to 100 range (with both upper and lower bounds).

The inventors also note that, as used herein, "coupled in communication" denotes a direct or indirect connection that permits the flow of solids and/or liquids. For example, the outlet of primary oxidation reactor 10 (FIG. 1) is "coupled in communication" with the inlet of solids recovery system 24, even though there is intermediate equipment (e.g., secondary oxidation reactor 114) located therebetween.

The invention has been described in detail with particular reference to preferred embodiments thereof, but will be understood that variations and modification can be affected within the spirit and scope of the invention.

We claim:

1. A process comprising:
   (a) providing a slurry comprising a solid phase and a liquid phase comprising a mother liquor, wherein said solid phase contains a first quantity of terephthalic acid, wherein said liquid phase contains a second quantity of terephthalic acid;
   (b) subjecting at least a portion of said first quantity of terephthalic acid to oxidation treatment to thereby produce oxidation-treated terephthalic acid; wherein said oxidation-treated terephthalic acid has a b* value of about 3.5 to about 10 and a 4-carboxybenzaldehyde (4-CBA) and para-toluic acid (p-TAc) content totaling greater than 700 ppmw; and
   (c) subjecting at least a portion of said mother liquor containing said second quantity of said terephthalic acid to evaporation treatment to form a concentrated slurry having more than about 10 weight % solid terephthalic acid particles, and subsequently subjecting said second quantity of terephthalic acid to hydrogenation treatment to thereby produce hydrogenation-treated terephthalic acid; wherein said hydrogenation-treated terephthalic acid has a b* value of less than 3.0 and a 4-CBA and p-TAc content totaling less than 700 ppmw; and;
   (d) combining at least a portion of said oxidation-treated terephthalic acid with at least a portion of said hydrogenation-treated terephthalic acid to produce a final composite acid suitable for use in the manufacture of polyesters; wherein the ratio of the amount of said oxygenation-treated terephthalic acid to said hydrogenation-treated terephthalic acid combined with one another is in the a range of from about 10:1 to about 1,000:1 by weight; wherein said process further comprises recovering solid particles of said second quantity of terephthalic acid prior to said hydrogenation treatment of step (c).

2. The process of claim 1 wherein said providing of step (a) includes oxidizing para-xylene in an initial oxidation reactor, wherein at least a portion of the evaporated mother liquor is recycled to said initial oxidation reactor.

3. The process of claim 1 wherein said process further comprises displacing at least a portion of said mother liquor from said concentrated slurry with a wash liquid.

4. The process of claim 3 wherein said providing of step (a) includes oxidizing para-xylene in an initial oxidation reactor, wherein at least a portion of the displaced mother liquor is recycled to said initial oxidation reactor.

5. The process of claim 1 wherein said process further comprises dissolving at least a portion of the recovered solid particles in a solvent to thereby form a hydrogenation solution, wherein said hydrogenation treatment of step (c) includes subjecting said hydrogenation solution to liquid-phase hydrogenation to thereby produce a hydrogenated solution containing said hydrogenation-treated terephthalic acid.

6. The process of claim 5 wherein said solvent contains at least about 50 weight percent water.

7. The process of claim 5 wherein said process further comprises recovering solid particles of said hydrogenation-treated terephthalic acid from said hydrogenated solution.

8. The process of claim 7 wherein said recovering of said solid particles of said hydrogenation-treated terephthalic acid particles is accomplished at least in part by cooling said hydrogenated solution.

9. The process of claim 7 wherein said process further comprises recovering solid particles of said oxidation-treated terephthalic acid, wherein said process further comprises combining at least a portion of the recovered particles of said hydrogenation-treated terephthalic acid with at least a portion of the recovered particles of said oxidation-treated terephthalic acid.

10. The process of claim 1 wherein said providing of step (a) includes oxidizing an oxidizable compound in an initial oxidation reactor, wherein step (b) is carried out in a secondary oxidation reactor that is separate from said initial oxidation reactor.

11. The process of claim 10 wherein said oxidizable compound is para-xylene.

12. The process of claim 1 wherein said slurry contains in the range of from about 5 to about 40 weight percent of said solid phase.

13. The process of claim 1 wherein said mother liquid phase contains an acid component, wherein said acid component is an organic monocarboxylic acid having 1-6 carbon atoms.

14. The process of claim 13 wherein said mother liquid phase contains an oxidation catalyst.

15. The process of claim 14 wherein said acid component is acetic acid, wherein said oxidation catalyst comprises cobalt, molybdenum, and/or bromine.

* * * * *